United States Patent
Clarke

(10) Patent No.: US 7,396,547 B2
(45) Date of Patent: Jul. 8, 2008

(54) ANTISEPTIC COMPOSITION

(76) Inventor: Paul Douglas Clarke, 29 Harley Street, London (GB) W1G 9QR ( * ) Notice: Subject to any disclaimer, the term of this patent is extended or adjusted under 35 U.S.C. 154(b) by 0 days.

(21) Appl. No.: 11/669,137

(22) Filed: Jan. 30, 2007

(65) Prior Publication Data

US 2007/0122499 A1    May 31, 2007

Related U.S. Application Data

(60) Division of application No. 11/233,362, filed on Sep. 23, 2005, now Pat. No. 7,189,421, which is a continuation-in-part of application No. 10/886,622, filed on Jul. 9, 2004, now abandoned, which is a division of application No. 10/031,170, filed as application No. PCT/GB00/02825 on Jul. 21, 2000, now abandoned.

(30) Foreign Application Priority Data

Jul. 21, 1999 (GB) ................................ 9917040.9

(51) Int. Cl.
*A61K 31/045* (2006.01)

(52) U.S. Cl. ........................................ 424/742; 514/738
(58) Field of Classification Search ................ None
See application file for complete search history.

(56) References Cited

OTHER PUBLICATIONS

Ginsberg and Spigelman (Nature Medicine (2007), vol. 13, No. 3, pp. 290-294).*

* cited by examiner

*Primary Examiner*—Susan C Hoffman
(74) *Attorney, Agent, or Firm*—Rankin, Hill & Clark LLP

(57) ABSTRACT p-Menthane-3,8-diol (PMD) has antiseptic, antibiotic, fungicidal and bactericidal properties. It is used for these purposes in the form of compositions and method comprising the PMD and optionally a carrier. A method of treating acne, folliculitis body, scalp folliculitis, Hydradinitis suppuritiva dandruff, seborrhoeic dermatitis (scalp or body), pityriasis versicolor, pityrosporun folliculitis, tinea corporis, tinea pedis, tinea cruris, tinea capitis, tinea unguum, tinea folliculitis or rosacea in a patient including administering an effective amount of PMD.

17 Claims, No Drawings

ANTISEPTIC COMPOSITION

CROSS-REFERENCE TO PATENT APPLICATIONS

This application is a division of U.S. application Ser. No. 11/233,362, filed Sep. 23, 2005, now U.S. Pat. No. 7,189,421, which application was a continuation in part of U.S. application Ser. No. 10/886,622, filed Jul. 9, 2004, now abandoned, which was a division of U.S. application Ser. No. 10/031,170, filed Feb. 4, 2002, now abandoned, which was filed as a U.S. National Stage application of PCT/GB00/02825, filed Jul. 21, 2000, and claims priority from GB9917040.9, filed Jul. 21, 1999, all of which are incorporated herein by reference in their entirety.

FIELD OF THE INVENTION

The present invention relates to an antiseptic composition.

BACKGROUND OF THE INVENTION

It is known that a number of natural products have insect repellent properties. Citronella oil, which is obtained from certain grasses is one example of such a natural product, and oil from the Neem tree is another. We have previously investigated certain insect repellent natural products and have found that the insect repellent properties are in a fraction rich in p-menthane-3,8-diol (PMD). This is described in our GB-A-2282534. In GB-A-1315625, there is described the use of certain p-menthane diols, but not PMD, to provide a physiological cooling effect.

SUMMARY OF THE INVENTION

We have now found, very surprisingly, that PMD not only has the insect repellent properties we have previously described, but also possesses the totally unrelated quality of antiseptic properties. Thus, we have observed antiseptic activity of the compound against certain microbes and, in particular and most importantly, against two strains of multiply resistant *Staphylococcus aureus* (MRSA). It appears, therefore, that PMD will have general antiseptic utility and be particularly useful, at least in respect of certain microbes, as a bactericide as well as being fungicidal and capable of acting as an antibiotic.

DETAILED DESCRIPTION OF THE PREFERRED EMBODIMENTS

According to one aspect of the invention, we provide the use of PMD as an antiseptic. According to a further aspect of the invention, there is provided the use of PMD as an antibiotic. According to a further aspect, the invention provides the use of PMD as a fungicide and/or bactericide.

The PMD for use in the present invention may be derived from a natural source or may be synthetic, or a mixture of the two. A preferred source of natural PMD is the lemon eucalyptus plant, *Eucalyptus citriodora*. Synthetic PMD may be obtained by any route, for example, such as described by Zimmerman and English in J.A.C.S. 75 (1953) pp 2367-2370. PMD is also a precursor obtained during the synthesis of menthol. The precursor is usually in the form of a specific isomer of PMD.

The PMD for use in the present invention may be a substantially pure form of the compound, or a crude extract, for example from a natural source. An example of a crude extract is a PMD-rich extract derived from lemon eucalyptus. The PMD can be produced by cyclisation of citronellal which is present in high concentration in lemon eucalyptus oil (approximately 75% by weight). We have obtained a PMD-rich extract from the lemon eucalyptus oil which includes both geometric isomers of PMD usually at about 64% by weight. The crude extract also includes citronellol and isopulegols plus certain other minor components.

According to a further aspect of the invention, there is provided the use of a PMD-rich extract containing composition, which extract is derived from natural lemon eucalyptus oil, as an antiseptic. We market this crude extract under the trade mark "Citriodiol".

It is known that eucalyptus oils include certain components, such as cineoles, which are known to have antiseptic properties. For the avoidance of doubt, we make no claim to the antiseptic activity of any component, other than PMD when it is derived from a natural source.

A composition for use in accordance with the invention can comprise PMD and a carrier. PMD is poorly soluble in water, so that it is preferred to use an oil as a carrier, or use a solvent, such as alcohol, for water-based compositions.

It is known that PMD exists in two geometric isomeric forms, namely the cis and trans isomers. Altogether, there are 8 isomers of PMD, as shown in structural formulas I through VIII. This invention encompasses any single one isomer and also any combination of one or more isomers."

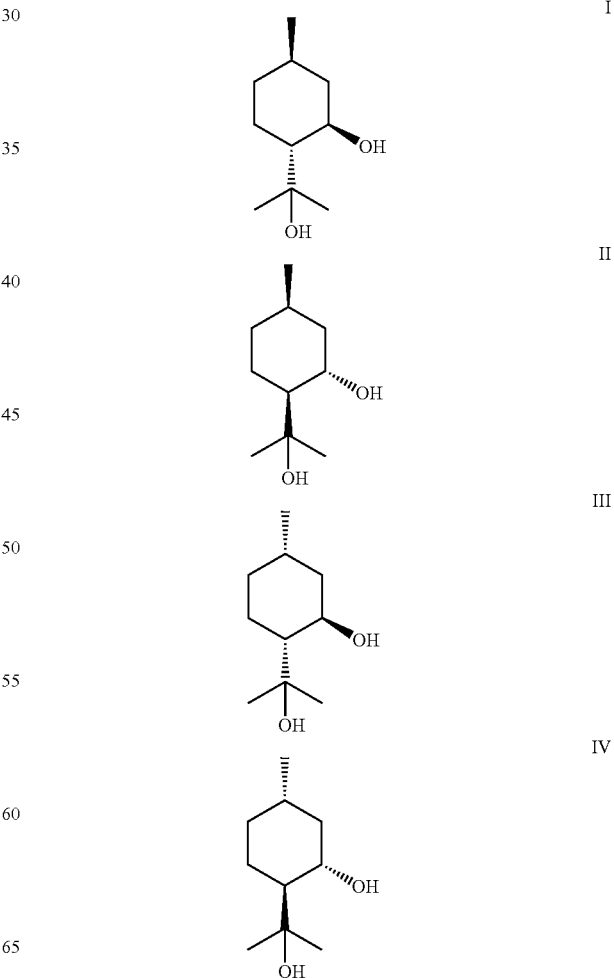

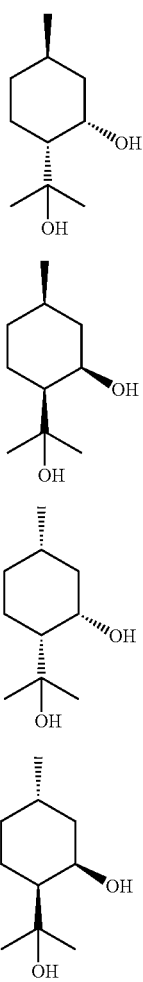

Our experimental work is based on a substantially pure racemic optical mixture of the cis isomer. It is, however, understood that the claimed activities for PMD are common to all its isomeric forms. Thus, the PMD may be used in the form of a single pure cis or trans isomer, or in the form of a mixture of the isomers, with any appropriate proportion of each isomer. PMD is normally produced in a mixture of cis:trans at about 2:1, and this mixture is perfectly acceptably. However, a 50:50 mixture of the cis and trans isomers may instead be used, as may other mixtures.

In a further aspect of the invention, the composition for use in the invention comprises only one of the isomers of PMD, with a carrier therefor.

It is a further aspect of the invention that the relative amounts of cis: trans PMD isomers in the compositions for use in the present invention are varied as desired. This can be done by mixing previously separated isomers in the appropriate ratio, or by adjusting the ratio in a mixture of naturally occurring or synthetic source.

In tests we have found that PMD is effective against certain strains of MRSA. In a further aspect, therefore, the invention provides the use of PMD against MRSA.

We have also found that PMD is effective against acne. The etiology of acne is not completely understood, but, in some instances, it is believed that acne has a bacterial etiology.

PMD is also suitable for treating other conditions/diseases where there is potential bacterial aetiology, such as folliculitis body, scalp folliculitis and Hydradinitis suppuritiva; conditions where there is potential antimicrobial plus antiparasitic action, such as rosacea; conditions where there is anti Malezezzia furfur activity, such as dandruff, seborrhoeic dermatitis (scalp and body), pityriasis versicolor and pityrosporun folliculitis; and conditions where there is antidermatophyte activity, such as tinea corporis, tinea pedis, tinea cruris, tinea capitis, tinea unguum and tinea folliculitis.

The uses of the present invention may be adopted in sanitizing a surface, for example in a hospital room or ward. In such cases PMD is applied to the surfaces. The PMD is preferably either in solution or as an emulsion in suitable liquid carriers. Most desirably, the PMD is formulated for spray application. For example, the PMD or Citriodiol can be dissolved in a suitable solvent or solvent mixture. In a particularly preferred mode of application, the spray is an electrostatic spray. For electrostatic spraying, the solvent or solvent system will need to be appropriate for electrostatic spraying, as will be clear to those skilled in the art. I prefer to use a mixture of conductive and non-conductive solvents to achieve a sprayable solution with the appropriate electrical resistivity for the spray nozzle in question, but suitable single solvents can of course be used. Charged particles of the composition including PMD are projected as a fine mist and because all the particles carry a similar, for example positive, charge they repel each other, but are attracted to an oppositely charged surface. By this means of spraying, a very good coverage of the composition on the surface may be obtained. Devices for electrostatically spraying the composition for use in the invention will be known to the person skilled in the art.

A spray may also be used, for example, for dispensing a composition including PMD onto a hand (or other part) of a person. The actuation of the dispenser may be by means of an infra-red sensor, for example, so that the person need not contact a surface, and thereby risk the transfer of microbes to or from their hand. Electrostatic spray application to a hand may be used, with advantage, where a substantially uniform coverage of antiseptic is particularly important e.g. to a surgeon during "scrubbing up" before surgery.

To increase the likelihood of the charged particles covering the skin surface, desirably the electrostatic spray nozzles may be arranged to spray into the interior of a cabinet or container as the hand is introduced therein.

The liquids for applying to a surface, by spraying or otherwise, in accordance with the invention may contain, apart from the solvent(s) and/or other liquid carrier(s), other components as necessary or desirable for the intended purpose. Thus, second or further antiseptics may be included, as may surfactants, fragrances etc. In general, the compositions may be identical to known compositions for the purpose except that they contain PMD in addition to, or in whole or part substitution for one or more of, the other ingredients. The amount of PMD can vary widely, the greater the amount the greater the effect. We prefer to use up to about 5% by weight of the composition, in general.

PMD may also be included as a component in household detergents, cleansers and creams, for example, washing powders or conditioners and hand gels.

Again, the PMD may be included in what are otherwise standard or known compositions for the purpose concerned. The PMD may be an extra ingredient or in partial or complete replacement of a standard ingredient. The compositions may already contain an antiseptic and the PMD is added to give an extra antiseptic effect.

Furthermore, PMD may be impregnated into household objects which may be prone to microbial infestation and so risk infecting inhabitants, e.g. dishcloths, plastic soap dishes, surfaces used for the preparation of food. For these purposes, the PMD may be included during manufacture of the object, e.g. in mixtures for plastics mouldings or the like, or it may be applied to the object after manufacture, e.g. by soaking dishcloths in PMD. The presence of the PMD at the surface of the object will provide the desired antiseptic effect. This is particularly useful for work surfaces, although of course such surfaces can also be regularly treated with PMD as by spraying or otherwise.

A composition including PMD can also be used in medicine. For example, it can be applied to broken skin, or to internal mucous membranes. It may be an ingredient in throat lozenges or pastilles or other products for ingestion. In this aspect, the invention provides PMD for use as an antiseptic, antibiotic, bactericide or fungicide. In medical uses the PMD may be formulated with the carrier as a cream, such as an acne cream, or, as mentioned above, as a throat lozenge or pastille. One cause of dandruff is known to be of fungal origin. PMD may be included as an ingredient in an anti-dandruff shampoo in order to combat the scalp infection, and indeed in non-medicated shampoos and the like. A further specific medical use is based upon the fact that many carriers of *staphylococcus* bacteria carry the bacterium in their nasal passages. A composition including PMD may be applied to the accessible inner surfaces of the nose in order to control or eliminate bacteria which may cause regular systemic effects. Another specific medical use is in wound irrigation during surgery, e.g. surgery conducted on the peritoneal cavity.

As will be evident to those skilled in the art, there are a very large number of medical uses of PMD not only as an antiseptic but also as an antibiotic, fungicide and bactericide. In general, new formulations for these purposes are not required: it is adequate and satisfactory to take a known or standard composition and include the PMD therein. Alternatively, one or more ingredients may be replaced by the PMD as appropriate. Those skilled in the art will well know the make-up of the various compositions and no further particular description thereof is given here.

PMD is the active ingredient in our MOSIGUARD™ insect repellant. We have conducted tests to show regulatory authorities that PMD is not toxic, and we have marketed our insect repellent for several years and there has been no report of any significant toxicity thereof. Potentially, therefore, the medical uses of PMD may be topical or systemic. Systemic administration may be by way of an oral dosage form or by a parenteral route, such as by intra-venous injection.

In a further aspect, the invention provides the use of PMD in the manufacture of an antiseptic, antibiotic or fungicidal medicament.

In general, PMD is used in accordance with the invention in a wide variety of vehicles, depending on the particular use intended. The vehicles may, for example, include solids, liquids, emulsions, foams and gels. Typical vehicles include aqueous or alcoholic solutions, oils, fats, fatty acid esters, long chain alcohols and silicone oils, finely divided solids such as starch or talc, cellulosic materials and aerosol propellants. Topical compositions include perfumes, powders and other toiletries, lotions, liniments, oils and ointments, for example. Toiletries generally include after shave lotions, shaving soaps, lipstick, creams, foams, toilet water, deodorants, antiperspirants, solid colognes, toilet soaps, bath oils and salts, shampoos, face and hand creams, cleansing tissues, mouthwashes, eye drops, for example. Medicaments and allied compositions include, for example, ointments, lotions, decongestants and throat lozenges.

Topical creams, such as acne creams, may be formulated with a combination of excipients suitable for providing a formulation comprising PMD as the active agent, and which does not significantly contribute further to the comedogenicity. Suitable excipients include: emollients, such as *Carthamus Tinctorius* (Safflower) seed oil and isononyl isononanoate; humectants/moisturisers/solvents, such as propylene glycol; spreading agents, such as diisopropyl adipate; surfactant systems, such as a combination of polysorbate 40 and sorbitan palmitate; skin conditioners, such as cyclopentasiloxane; emulsion stabilisers, such as cetearyl alcohol; reological modifiers/thickeners, such as carbomer; antioxidants, such as tocopherol; pH adjusters, such as triethanolamine; and collating agents, such as disodium EDTA.

The amount of PMD present in the compositions will be selected to give the desired effect but we believe that generally from 0.5 to 5% by weight will be satisfactory. Greater or lesser amounts can be used.

A PMD-rich extract may be obtained from PMD-containing material, such as the leaves of a eucalyptus plant. A preferred source of PMD rich extract is obtained by stirring eucalyptus citriadora oil derived from the plant with dilute sulphuric acid (usually 5% sulphuric acid), as previously explained in our GB-A-2282534.

In order that the invention may be fully understood, the following Example is given by way of illustration only.

EXAMPLE 1

Cis PMD MIC/MBC Determination

MIC—minimum inhibitory concentration. This is the concentration of PMD which prevents bacterial growth. A "+" indicates bacterial growth, whereas a "−" indicates that bacterial growth is prevented. Thus, for *E. Coli* below, the minimum inhibitory concentration is 0.25% PMD in 1.25% ethanol.

MBC—minimum bactericidal concentration. This is the concentration of PMD which kills the bacteria. A "✚" indicates live bacteria are present. Therefore, for *E. Coli*, the minimum bactericidal concentration is 0.5% PMD in 2.5% ethanol i.e. the concentration immediately above that which does not kill the bacteria.

Cis PMD was dissolved in Absolute Ethanol (0.2 g/ml) to give 20% solution. This was further diluted in water to give 10% in 50% EtOH. 200 μl was added to 0.8 ml Iso-sensitest broth to give a 2% solution in 10% EtOH. Serial 2-fold dilutions in ISB were then carried out and 20 μl *E. coli* (McFarlane 0.5) were added to each tube and incubated overnight at 37° C. After 18 hours, tubes showing no growth were sub-cultured.

| Sample | Percentage Compositions | | | | | |
|---|---|---|---|---|---|---|
| | 2 | 1 | 0.5 | 0.25 | 0.125 | 0.06 |
| E. coli | − | − | − | −✚ | +✚ | +✚ |
| S. aureus (oxford) | − | − | −✚ | +✚ | +✚ | +✚ |
| P. aeruginosa | − | − | −✚ | +✚ | +✚ | +✚ |
| MRSA 15 | − | − | −✚ | +✚ | +✚ | +✚ |
| MRSA 16 | − | − | −✚ | +✚ | +✚ | +✚ |
| S. pyogenes | − | − | − | −✚ | +✚ | +✚ |
| Alcohol concentration | 10% | 5% | 2.5% | 1.25% | 0.6% | 0.3% |
| Control: Alcohol only/E. coli | | ✚ | ✚ | ✚ | ✚ | ✚ |

EXAMPLE 2

A composition of the invention for application to sanitise a surface was made up: by dissolving Citriodiol in a mixture of cyclohexanane (40%) and Exxol D (59%). The composition was applied by electrostatic deposition and by non-electrostatic spraying, to provide a thin antiseptic covering on various surfaces (human skin and work surfaces). The amounts of Citriodiol were varied to provide from about 0.5% to 5.00% PMD. Good antiseptic properties were obtained.

EXAMPLE 3

A composition of the invention for application to sanitise a surface was made by dissolving Citriodiol in a mixture of:

| | |
|---|---|
| *Downal PnB (20%) | 667 ml |
| **Isopar L (44%) | 1473 ml |
| Stalox 60 (6%) | 194 ml |

*Dowanol is a glycol ether/ether acetate solvent.
**Isopar is an isoparaffinic solvent.

The amount of Citriodiol was initially 1000 ml of 30% Citriodiol but other amounts can also be used.

The solution was sprayed electrostatically and nonelectrostatically onto various surfaces, e.g. the hands, planar work surfaces, etc. with very satisfactory results.

EXAMPLE 4

A simple hair shampoo of sodium lauryl ether sulphate (10%) dispersed in water (90%) was mixed with 2% PMD to provide antiseptic properties in the shampoo. Other shampoos, including medicated shampoos for dandruff treatment, can also have PMD incorporated therein to provide an antiseptic, or enhanced antiseptic, effect.

EXAMPLE 5

Standard proprietary toilet soap formulations can be modified by the inclusion of from ½ to 5% PMD therein to provide an antiseptic or enhanced antiseptic effect. In general, it is not necessary to use more than 5% PMD but greater amounts can be used if desired.

EXAMPLE 6

A dermatological cream base of composition

| | % |
|---|---|
| sodium citrate | 1 |
| cetyl alcohol | 2 |
| stearyl alcohol | 3 |
| glycerine | 12 |
| sodium lauryl sulphate | 5 |
| parabens | 0.3 |
| petrolatum album to | 100% | can be modified in accordance with the invention by including up to about 5% PMD therein to provide antiseptic properties therein.

EXAMPLE 7

Aqueous nose drops made from a basic aqueous nose drop composition, e.g.

| | |
|---|---|
| sodium hyaluronate | 0.01 g |
| sodium cromoglycate | 1.0 g |
| sterile purified water to | 100 ml |
| acid to pH 5.0 | | can be modified in accordance with the invention to include PMD therein, e.g. 0.5%-1%, to impart a further antiseptic effect.

EXAMPLE 8

Standard antiseptic solutions can have their effect enhanced by including therein PMD, in accordance with the invention. The PMD may be added to the standard solutions, or it may be used as a replacement for another antiseptic therein. Antiseptic solutions are generally fairly complex mixtures of antimicrobials, surfactants and solvents, but PMD can be formulated relatively simply in a suitable solvent to provide antiseptic properties.

EXAMPLE 9

Sterile antiseptic solutions for use internally on the human body, for example in wound sites during surgery, can be made using PMD in place of or in addition to other antiseptics. Such solutions are very effective for wound treatment or ensure antisepsis.

EXAMPLE 10

Sterile surgical scrubs can be made including PMD as the, or one of the, antiseptics. For example, PMD may be included in a known scrub such as Hibitane which comprises a detergent base of polyoxyethylene-polyoxypropylene block polymer (a nonionic surfactant) and dimethyllauryl amine oxide (an amphoteric surfactant), and chlorhexidine digluconate as the antiseptic. In general, PMD can be used with, or in place of, known antiseptics such as chlorhexidine and others, as will be clear to those skilled in the art.

EXAMPLE 11

A topical cream of the invention was made as follows.

| Ingredient | Weight % Total |
|---|---|
| Aqua (water) | 74.93 |
| *Carthamus Tinctorius* (Safflower) Seed Oil | 5 |
| Propylene Glycol | 5 |
| Diisopropyl Adipate | 4 |
| Polysorbate 40 | 2.25 |
| Sorbitan Palmitate | 2.25 |
| Cyclopentasiloxane | 2 |
| PMD (in the form of Citriodiol) | 2 |
| Cetearyl Alcohol | 1 |
| Isononyl Isononanoate | 1 |
| Carbomer | 0.3 |
| Tocopherol | 0.1 |
| Triethanolamine | 0.09 |
| Disodium EDTA | 0.08 |

It is apparent that embodiments other than those expressly described above may come within the spirit and scope of the present invention. Thus, the present invention is not defined by the above-provided description, but rather is defined by the claims appended hereto.

The invention claimed is:

1. A method of treating a bacterial infection in a patient comprising administering an antibacterially effective amount of PMD to the patient, wherein the bacterial infection is caused by *Staphylococcus aureus*.

2. The method according to claim 1, wherein the PMD is provided as part of a composition including PMD and a carrier.

3. The method according to claim 2, wherein the amount of PMD in the composition is greater than 0.5 wt %.

4. The method according to claim 2, wherein the amount of PMD in the composition is from 0.5 wt % to 5 wt %.

5. The method according to claim 2, wherein the composition is selected from the group consisting of shampoos, ointments, lotions, creams, lipstick, throat lozenge, pastille, nasal spray, surgical irrigation composition, mouthwash, decongestants, eye drops, perfumes, powders, after shave lotions, foams, toilet water, and solid colognes.

6. The method according to claim 2, wherein the composition is a topical cream.

7. The method according to claim 6, wherein the topical cream is formulated with a combination of excipients suitable for providing a formulation which does not significantly contribute further to comedogenicity.

8. A method of treating a bacterial infection in a patient comprising administering an antibacterially effective amount of PMD to the patient, wherein the bacterial infection is selected from the group consisting of acne, body folliculitis, scalp folliculitis, Hidradenitis suppurativa and rosacea.

9. The method according to claim 8, wherein the PMD is provided as part of a composition including PMD and a carrier.

10. The method according to claim 9, wherein the amount of PMD in the composition is greater than 0.5 wt %.

11. The method according to claim 9, wherein the amount of PMD in the composition is from 0.5 wt % to 5 wt %.

12. The method according to claim 9, wherein the composition is selected from the group consisting of shampoos, ointments, lotions, creams, lipstick, perfumes, powders, after shave lotions, foams, toilet water, and solid colognes.

13. The method according to claim 9, wherein the composition is a topical cream.

14. The method according to claim 13, wherein the topical cream is formulated with a combination of excipients suitable for providing a formulation which does not significantly contribute further to comedogenicity.

15. A method of treating a topical condition caused by a bacterial infection in a patient comprising administering an antibacterially effective amount of PMD to the patient, wherein the bacterial infection is selected from the group consisting of acne, body folliculitis, scalp folliculitis, Hidradenitis suppurativa and rosacea.

16. A method of treating rosacea comprising administering an effective amount of PMD to a patient in need thereof.

17. A method of treating acne comprising administering an effective amount of PMD to a patient in need thereof.

* * * * *